US012629196B2

(12) United States Patent
Govari et al.

(10) Patent No.: US 12,629,196 B2
(45) Date of Patent: May 19, 2026

(54) ABLATION PULSE GENERATOR WITH PARALLEL POWER BANK

(71) Applicant: BIOSENSE WEBSTER (ISRAEL) LTD., Yokneam (IL)

(72) Inventors: Assaf Govari, Haifa (IL); Andres Claudio Altmann, Haifa (IL); Yuri Shamis, Haifa (IL); Lilah Marziano, Ganey-Tivka (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 535 days.

(21) Appl. No.: 18/089,228

(22) Filed: Dec. 27, 2022

(65) Prior Publication Data

US 2024/0206943 A1    Jun. 27, 2024

(51) Int. Cl.
| | |
|---|---|
| *A61B 18/12* | (2006.01) |
| *A61B 17/00* | (2006.01) |
| *A61B 18/00* | (2006.01) |
| *H02J 7/90* | (2026.01) |

(52) U.S. Cl.
CPC .............................. *A61B 18/1206* (2013.01); *A61B 2017/00172* (2013.01); *A61B 2018/00577* (2013.01); *A61B 2018/0072* (2013.01); *A61B 2018/00779* (2013.01); *A61B 2018/00892* (2013.01); *A61B 2018/1226* (2013.01); *H02J 7/927* (2026.01)

(58) Field of Classification Search
CPC ........... A61B 2017/00172; A61B 2018/00577; A61B 2018/0072; A61B 2018/00779; A61B 2018/00892; A61B 2018/1226; A61B 2018/00767; A61B 18/1206; H02J 7/00711; H02J 7/927

USPC ........................................................... 606/34
See application file for complete search history.

(56) References Cited

U.S. PATENT DOCUMENTS

| | | | |
|---|---|---|---|
| 5,391,199 | A | 2/1995 | Ben Haim |
| 5,443,489 | A | 8/1995 | Ben-Haim |
| 5,558,091 | A | 9/1996 | Acker |
| 6,172,499 | B1 | 1/2001 | Ashe |

(Continued)

FOREIGN PATENT DOCUMENTS

| | | |
|---|---|---|
| CN | 113749759 A | 12/2021 |
| KR | 2326448 B1 | 11/2021 |

(Continued)

OTHER PUBLICATIONS

Translation of KR102326448 (Year: 2021).*
European Search Report for corresponding EPA No. 23219910.9 dated May 22, 2024.

*Primary Examiner* — Beverly M Flanagan

(57) ABSTRACT

An apparatus (50) for generating ablation pulses includes a pulse generator (102), a power supply (104), a sensing circuit (110), and an energy storage power bank (108). The pulse generator is configured to generate ablation pulses for ablation of tissue. The power supply is configured to supply electrical power to the pulse generator. The sensing circuit is configured to sense a weakening of the electrical power supplied by the power supply to the pulse generator. The energy storage power bank is connected in parallel with the power supply, and is configured to supply to the pulse generator, responsively to an indication from the sensing circuit indicative of the weakening, additional current that augments a current supplied by the power supply.

18 Claims, 4 Drawing Sheets

(56)                  References Cited

U.S. PATENT DOCUMENTS

| | | | |
|---|---|---|---|
| 6,239,724 B1 | 5/2001 | Doron | |
| 6,332,089 B1 | 12/2001 | Acker | |
| 6,484,118 B1 | 11/2002 | Govari | |
| 6,618,612 B1 | 9/2003 | Acker | |
| 6,690,963 B2 | 2/2004 | Ben Haim | |
| 6,788,967 B2 | 9/2004 | Ben Haim | |
| 6,892,091 B1 | 5/2005 | Ben Haim | |
| 7,536,218 B2 | 5/2009 | Govari et al. | |
| 7,756,576 B2 | 7/2010 | Levin | |
| 7,848,787 B2 | 12/2010 | Osadchy | |
| 7,869,865 B2 | 1/2011 | Govari et al. | |
| 8,456,182 B2 | 6/2013 | Bar-Tal et al. | |
| 10,673,347 B2 | 6/2020 | Sarnago Andia et al. | |
| 10,779,849 B2 | 9/2020 | Shelton, IV et al. | |
| 10,869,713 B2 | 12/2020 | Govari | |
| 2019/0350647 A1* | 11/2019 | Ramberg | A61N 1/327 |
| 2020/0289185 A1 | 9/2020 | Forsyth | |
| 2022/0278674 A1 | 9/2022 | Cadossi | |
| 2023/0240746 A1* | 8/2023 | Gundert | A61B 18/1492 |
| | | | 606/35 |

FOREIGN PATENT DOCUMENTS

| | | | | |
|---|---|---|---|---|
| KR | 102326448 B1 * | 11/2021 | ......... | A61B 18/1233 |
| WO | WO-2022164750 A1 * | 8/2022 | ......... | A61B 18/1492 |

* cited by examiner

ABLATION PULSE GENERATOR WITH PARALLEL POWER BANK

FIELD OF THE DISCLOSURE

The present disclosure relates generally to medical devices, and particularly to methods and systems for supplying operating power to an Irreversible Electroporation (IRE) pulse generator.

BACKGROUND OF THE DISCLOSURE

Tissue ablation is used in various medical procedures, such as in treating arrhythmias in a patient heart by a physician using one or more ablation catheters for generating a lesion at a predefined site within the patient heart, using high energy electric pulses.

Ablation is sometimes done using Irreversible Electroporation (IRE), also referred to as Pulsed Field Ablation (PFA), in which a generator applies high energy electric pulses to a patient's tissue. The pulses are applied in bursts, and the generator requires a significant amount of electric energy during the bursts.

The present disclosure will be more fully understood from the following detailed description of the examples thereof, taken together with the drawings in which:

DETAILED DESCRIPTION OF EXAMPLES

Overview

Pulsed Field Ablation (PFA) may be used for treating arrhythmia in a patient heart using one or more catheters having suitable electrodes. PFA may be used for ablating tissue cells by applying to the tissue high-voltage pulses. Cellular destruction occurs when the transmembrane potential exceeds a threshold, leading to cell death and irreversible electroporation (IRE) of the tissue, resulting in the formation of a lesion in a respective section of the heart. In PFA-based ablation procedures, a sequence of microsecond high-voltage electrical pulses is applied to the tissue intended to be ablated.

PFA pulses are typically administered in bursts of high voltage unipolar or bipolar pulses. In one example, the bursts typically last between 100 and 200 milliseconds, and the gap between bursts is typically between one and four seconds. The voltage of each pulse is typically between 500V and 2,000V, e.g., 1600-1800 V, and the current, depending on the impedance of the ablated tissue, is 10-80 Amps, but may optionally reach higher values. The pulse generator in this example requires 28 Volts DC and 80 Amps (2.24 KW) during delivery of the burst. The above values are chosen purely by way of example, and any other suitable values can be used in alternative examples. In any case, a power supply that meets such power levels may be expensive and bulky.

Examples of the present disclosure that are described hereafter provide techniques for using a power supply with rating that is below the requirement of the ablation pulse generator, wherein, during bursts, the power is augmented by a power-bank circuit. During the time intervals between the bursts, the power supply charges the power bank.

In some examples, the ablation pulse generator, the power-supply and the power bank are connected in parallel to a common power bus. In an example, the power bank comprises a sensing circuit that is coupled to the power bus, and indicates when the voltage on the power bus weakens; the power-bank circuit is configured to deliver, responsively to such indication, additional electric power to the ablation pulse generator.

In some examples, the sensing circuit monitors the voltage on the power bus and indicates voltage weakening if the voltage is below a preset threshold. In other examples, the sensing circuit measures a voltage decline rate on the power bus, and indicates voltage weakening if the weakening rate is exceeds a preset threshold.

In summary, the disclosed techniques enable using a compact, off the shelf, power supply to provide the power of a high power ablation pulse generator, using a power bank that is charged between bursts of pulses, and using a sensing circuit to detect when the power bank is to augment the current that the power supply delivers, so as to meet the ablation pulse generator requirements.

System Description

Figure 1:
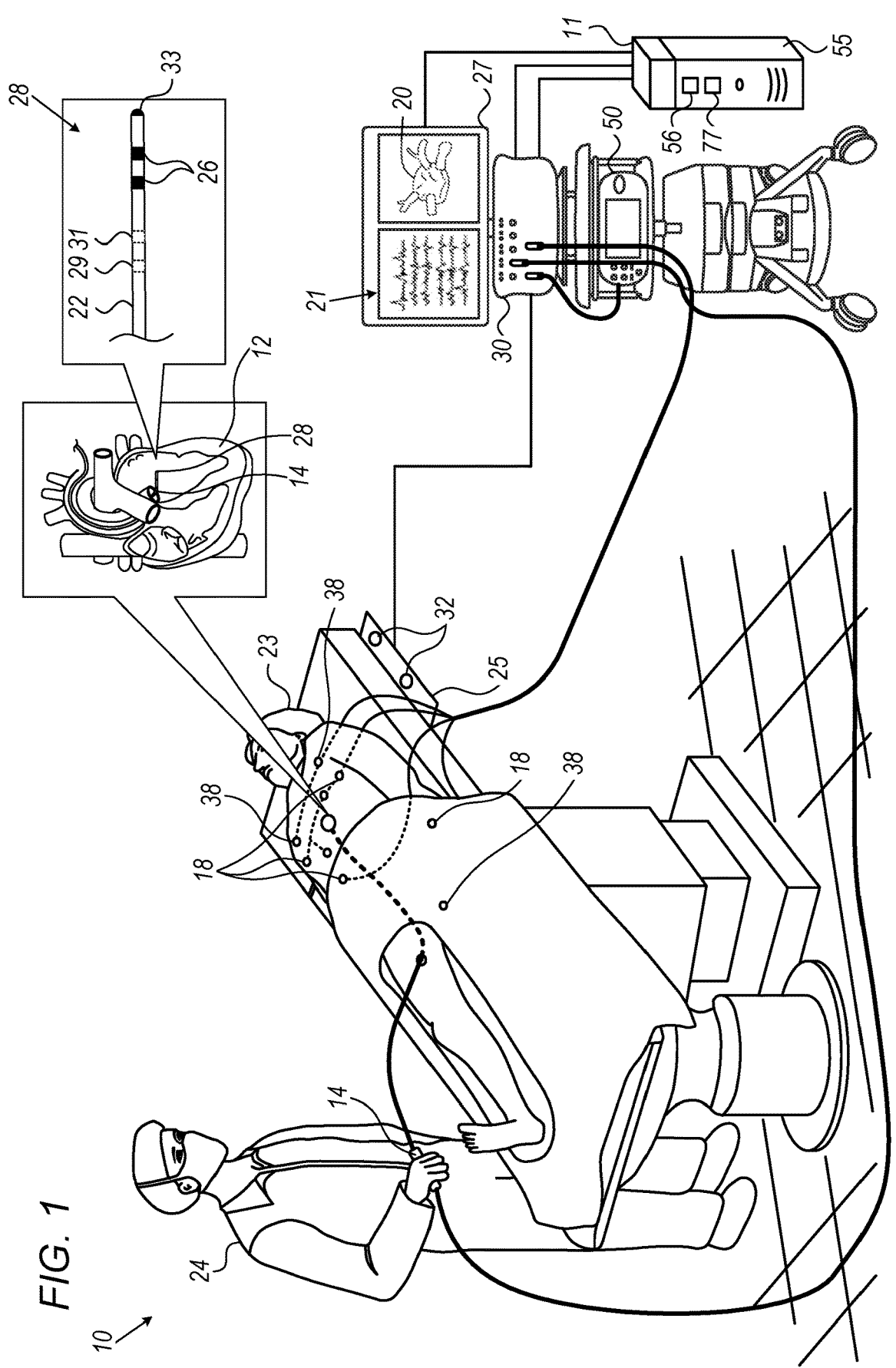
FIG. 1 is a schematic, pictorial illustration of a catheter-based electrophysiology mapping and ablation system, in accordance with an example of the present disclosure.

FIG. 1 is a schematic, pictorial illustration of a catheter-based electrophysiology mapping and ablation system 10, in accordance with an example of the present disclosure.

In some examples, system 10 includes multiple catheters, which are percutaneously inserted by a physician 24 through the patient's vascular system into a chamber or vascular structure of a heart 12. Typically, a delivery sheath catheter is inserted into the left or right atrium near a desired location in heart 12. Thereafter, one or more catheters can be inserted into the delivery sheath catheter so as to arrive at the desired location within heart 12. The plurality of catheters may include catheters dedicated for sensing Intracardiac Electrogram (IEGM) signals, catheters dedicated for ablating and/or catheters adapted to carry out both sensing and ablating. In some examples, physician 24 may place a distal tip 28 of catheter 14 in contact with the heart wall for sensing a target site in heart 12. Additionally, or alternatively, for ablation, physician 24 would similarly place a distal end of an ablation catheter in contact with a target site for ablating tissue intended to be ablated.

In the present example, catheter 14 includes one and preferably multiple electrodes 26 optionally distributed along a shaft 22 at distal tip 28 of catheter 14. Electrodes 26 are configured to sense the IEGM signals. Catheter 14 may additionally include a position sensor 29 embedded in or near distal tip 28 for tracking position and orientation of distal tip 28. Optionally and preferably, position sensor 29 is a magnetic based position sensor including three magnetic coils for sensing three-dimensional (3D) position and orientation.

In some examples, magnetic based position sensor 29 may be operated together with a location pad 25 including a plurality of (e.g., three) magnetic coils 32 configured to generate a plurality of (e.g., three) magnetic fields in a predefined working volume. Real-time position of distal tip 28 of catheter 14 may be tracked based on magnetic fields generated with location pad 25 and sensed by magnetic based position sensor 29. Details of the magnetic based position sensing technology are described, for example, in U.S. Pat. Nos. 5,5391,199; 5,443,489; 5,558,091; 6,172,499; 6,239,724; 6,332,089; 6,484,118; 6,618,612; 6,690,963; 6,788,967; 6,892,091.

In some examples, catheter 14 includes a contact force sensor 31, which is configured to sense the contact force applied to tissue of heart 12 by distal tip 28, and to produce a signal indicative of the sensed contact force.

In some examples, system 10 includes one or more electrode patches 38 positioned for skin contact on patient 23 to establish location reference for location pad 25 as well as impedance-based tracking of electrodes 26. For imped-ance-based tracking, electrical current is directed toward electrodes 26 and sensed at electrode skin patches 38 so that the location of each electrode can be triangulated via the electrode patches 38. This technique is also referred to herein as Advanced Current Location (ACL) and details of the impedance-based location tracking technology are described in U.S. Pat. Nos. 7,536,218; 7,756,576; 7,848, 787; 7,869,865; and 8,456,182. In some examples, the magnetic based position sensing and the ACL may be applied concurrently, e.g., for improving the position sens-ing of one or more electrodes coupled to a shaft of a rigid catheter or to flexible arms or splines at the distal tip of another sort of catheter, such as the PentaRay® or OPTRELL® catheters, available from Biosense Webster, Inc., 31A Technology Drive, Irvine, CA 92618.

In some examples, a recorder 11 displays electrograms 21 captured with body surface ECG electrodes 18 and intrac-ardiac electrograms (IEGM) captured with electrodes 26 of catheter 14. Recorder 11 may include pacing capability for pacing the heart rhythm and/or may be electrically con-nected to a standalone pacer.

In some examples, system 10 may include an ablation energy generator 50 that is adapted to conduct ablative energy to one or more of electrodes at a distal tip of a catheter configured for ablating. In the present example, Energy produced by ablation energy generator 50 includes pulse trains of pulsed-field (PFA) energy, including monopo-lar or bipolar high-voltage DC pulses as may be used to effect irreversible electroporation (IRE), or combinations thereof. In the present example, catheter 14 includes an ablation electrode 33 but optionally includes multiple elec-trodes 33 (not shown), positioned at distal tip 28 and configured to apply the pulse trains of PFA energy to tissue of the wall of heart 12.

In some examples, patient interface unit (PIU) 30 is an interface configured to establish electrical communication between catheters, electrophysiological equipment, power supply and a workstation 55 for controlling the operation of system 10. Electrophysiological equipment of system 10 may include for example, multiple catheters, location pad 25, body surface ECG electrodes 18, electrode patches 38, ablation energy generator 50, and recorder 11. Optionally and preferably, PIU 30 additionally includes processing capability for implementing real-time computations of loca-tion of the catheters and for performing ECG calculations.

In some examples, workstation 55 includes a storage device, a processor 77 with suitable random-access memory, or storage with appropriate operating software stored therein, an interface 56 configured to exchange signals of data (e.g., between processor 77 and another entity of system 10) and user interface capability. Workstation 55 may pro-vide multiple functions, optionally including (1) modeling the endocardial anatomy in three-dimensions (3D) and ren-dering the model or anatomical map 20 for display on a display device 27, (2) displaying on display device 27 activation sequences (or other data) compiled from recorded electrograms 21 in representative visual indicia or imagery superimposed on the rendered anatomical map 20, (3) dis-playing real-time location and orientation of multiple cath-eters within the heart chamber, and (4) displaying on display device 27 sites of interest such as places where ablation energy has been applied. One commercial product embody-ing elements of the system 10 is available as the CARTO™ 3 System, available from Biosense Webster, Inc., 31A Tech-nology Drive, Irvine, CA 92618.

In some examples, processor 77 receives from contact force sensor 31 a signal indicative of the contact force applied between ablation electrode 33 and the tissue intended to be ablated. Moreover, processor 77 may store one or more contact force thresholds in order to provide physician 24 with an indication of whether the contact force applied between ablation electrode 33 and the tissue intended to be ablated is sufficient.

Figure 2:
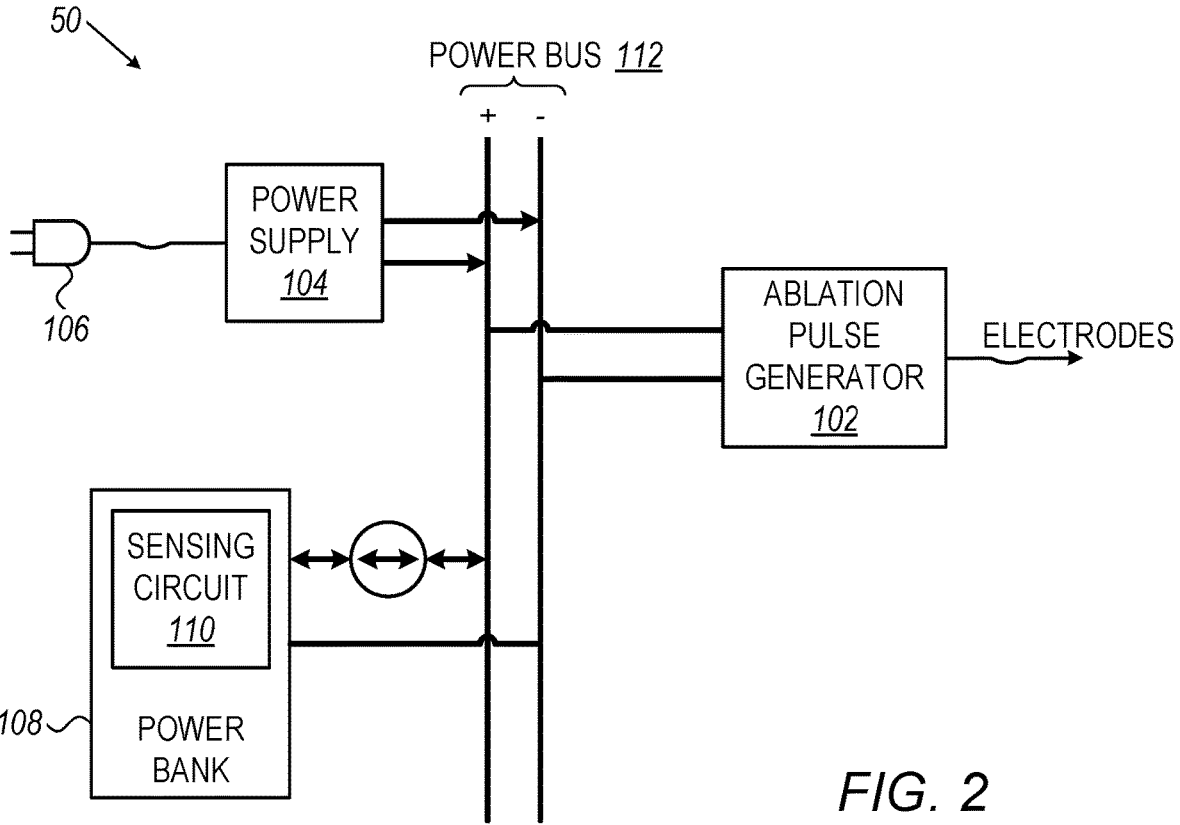
FIG. 2 is a block diagram that schematically illustrates an Ablation Energy Delivery circuit, in accordance with an example of the present disclosure.

FIG. 2 is a block diagram that schematically illustrates an Ablation Energy Generator 50, in accordance with an example aspect of the present disclosure. The ablation energy generator 50 comprises an Ablation Pulse Generator 102 that is configured to send high energy ablation pulses to the electrodes at the distal tip of a catheter configured for ablating, a Power Supply 104 that is operably coupled to an AC Power Cord 106, a Power-Bank 108. The power-bank comprises a Sensing Circuit 110.

According to the example aspect illustrated in FIG. 2, Ablation Energy Generator 50 further includes a Power-Bus 112, comprising a positive conductor and a negative con-ductor and connected in parallel to ablation pulse generator 102, to power supply 104, to power-bank 108 and, in the power-bank, to sensing circuit 110. It should be noted that power-bus 112 is not necessarily a physical component, rather, the power bus refers to the aggregation of all parallel supply wires that connect the supply terminal of the ablation pulse generator, the power supply, the power-bank, and the sensing circuit.

According to the example aspect illustrated in FIG. 2, the ablation pulses that ablation pulse generator 102 delivers comprise 100-200 milliseconds bursts of positive and nega-tive 100-200 micro-second pulses, one to four seconds apart, wherein in each pulse the generator delivers up to 80 A, at a voltage level between (typically) 500V and 2,000V, and wherein the time interval between bursts is one to four seconds. Other suitable voltages, current and times may be used in other example aspects.

Ablation pulse generator 102 may consume high power (e.g., 2.5 KW) when delivering a burst of pulses, and close to zero between the bursts. The average (over time) power that the ablation pulse generator consumes is significantly lower. For example, assuming 200 millisecond bursts every second, the average power is 2.5 KW×0.2=0.5 KW. Depend-ing on the ablation pulses, the power requirement of the ablation pulse generator may sometimes exceed the maxi-mum output rating of the power supply.

In an aspect, power bank 108 comprises capacitors to store energy (in the form of electric charge), for example, between the bursts, and to output the energy during the bursts, augmenting the current that power supply 104 gen-erates during bursts of ablation pulses. When the power generated by the power supply is larger than the power consumed by the ablation pulse generator (e.g., between bursts of pulses), the power bank accumulates energy.

Power bank 108 drives power onto power bus 112 responsively to an Activate indication that sensing circuit 110 sends to indicate a weakening of the power supplied to the ablation pulse generator. According to the example illustrated in FIG. 2, sensing circuit 110 is in power bank 108; in alternative example, the sensing circuit may be external to the power bank. According to an aspect of the example, the sensing circuit is configured to send the activate indication when the voltage level on power-bus 112 falls below a preset level. According to another aspect of the example, the sensing circuit sends the activate indication when the rate of decline of the voltage on the power bus is above a preset threshold; in yet other aspects any other suitable criterion may be used.

According to some aspects, power bank 108 may comprise one or more capacitors that store charge sourced by the power supply 104 (and delivered over power-bus 108). Any suitable type of capacitors may be used, including, for example, aluminum electrolytic capacitors and supercapacitors. According to an aspect, to receive high density, power-bank 108 comprises high voltage power capacitors for better energy storage density, including suitable up and down voltage converters for charging and discharging the capacitor.

The configuration of ablation pulse generator 50, illustrated in FIG. 2 is an example configuration that is cited merely for the sake of conceptual clarity. Other configurations may be used in other examples of the present disclosure. In an aspect, for example, sensing circuit 110 senses the current that power-supply 104 outputs and indicates "Activate" to the power bank responsively to the current output from the power supply (and, hence, sense circuit 110 may be embedded in power supply 104). In another example, the ablation pulses that ablation pulse generator 102 outputs may be current pulses at a preset current rating rather than voltage pulses.

In some examples, the power bank comprises a plurality of capacitors and a set of switches; when the power supply charges the power-bank, the switches connect the capacitors in parallel; when the power bank is to augment the current output by the power supply, the switches connect the switches in series to generate a higher voltage, which can then supply current to the power bus, e.g., though a current source.

Figure 3:
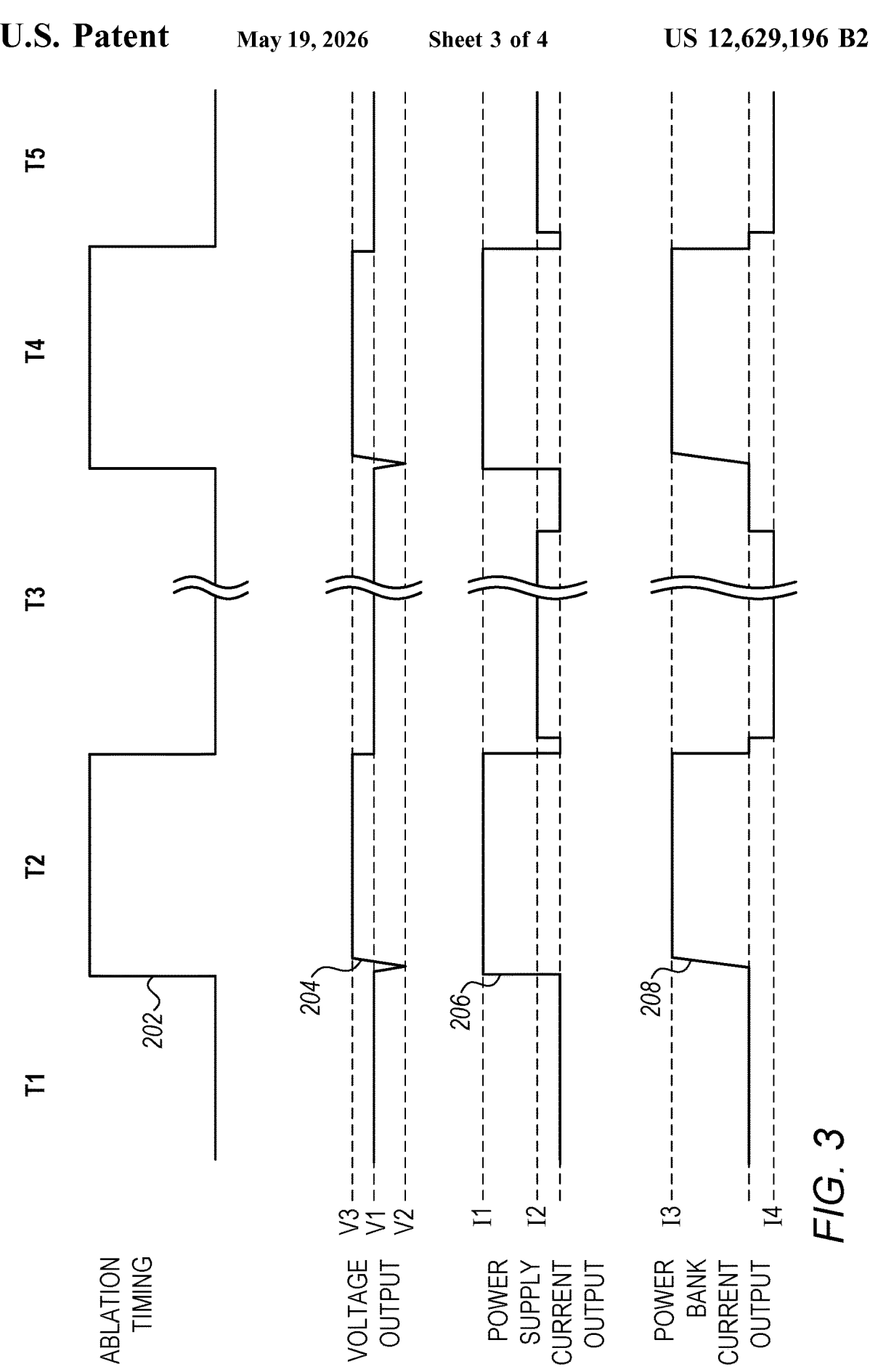
FIG. 3 is a timing waveform diagram that schematically illustrates the waveforms of signals in the ablation energy delivery circuit, in accordance with an example of the present disclosure.

FIG. 3 is a timing waveform diagram 200 that schematically illustrates the waveforms of signals in ablation energy generator 50 (FIG. 2), in accordance with an example of the present disclosure.

The time axis in FIG. 3 is divided to five discrete periods, designated T1 to T5 (T4 and T5 will not be described below; they are shown merely to better illustrate that the waveforms are repetitive; T4 is like T2, and T5 is like T3).

A curve 202 indicates when the ablation pulse generator generates ablation pulses. (We will refer below to the periods in which the generator generates ablation pulses as "Ablation periods", or "Ablation"; and to the gaps between ablation periods as "Gap periods", or "Gaps".)

A curve 204 shows the voltage level on the power bus ("Output Voltage"); a curve 206 depicts the power supply current; and a Curve 208 illustrates the current output of the power bank.

T1 is an initial gap period. The power bank is fully charged. The currents that the power supply and the power bank output are zero. The voltage on the power bus is designated V1 (e.g., 28V).

During T2, the ablation pulse generator generates ablation pulses and consumes a high supply current. The power supply current 206 rises to I1 (e.g., 50 A), which may be below the requirements of the ablation pulse generator (for example, 80 A). As a result, output voltage 204 momentarily drops to V2. In some examples V2=27V, which is below V2, but still safely within the minimum power-supply voltage specifications of the ablation pulse generator.

The power sense circuit may monitor the output voltage and indicate to the power bank that the voltage is below V2; the power bank, responsively, will deliver the charge accumulated in the power bank to the power bus (and, thence, to the ablation power generator). The power bank now outputs I3; in an example, I3=30 A, complementing the current that the power supply outputs (50 A) to 80 A—the requirement of the ablation pulse generator. The voltage 204 during T2 designated to V3 be (e.g., 29V) which is above V2 to compensate for reduction in voltage over the cable extending from the generator to the electrodes at the distal end of the catheter T3 is a Gap period. The ablation power supply current consumption drops to zero (or close to zero). After a short period in which the power supply output current 206 drops to zero, the power supply charges the power bank, and the power supply output current rises to I2 (e.g., 5 A). The current that the power bank outputs will, accordingly, drop to −5 A (negative values mean that the power bank receives rather than outputs current).

When the power bank is fully charged, charging will cease, the power supply and the power bank output currents will turn to zero (or close to zero). For proper operation, the charging should be completed within T3 and before the next ablation period.

All voltages, currents and time periods mentioned above with reference to FIG. 3 are cited by way of example. Other suitable voltages, currents and times may be used in alternative examples. In some examples, the charging of the power bank is gradual, for example, following an RC charge curve.

Figure 4:
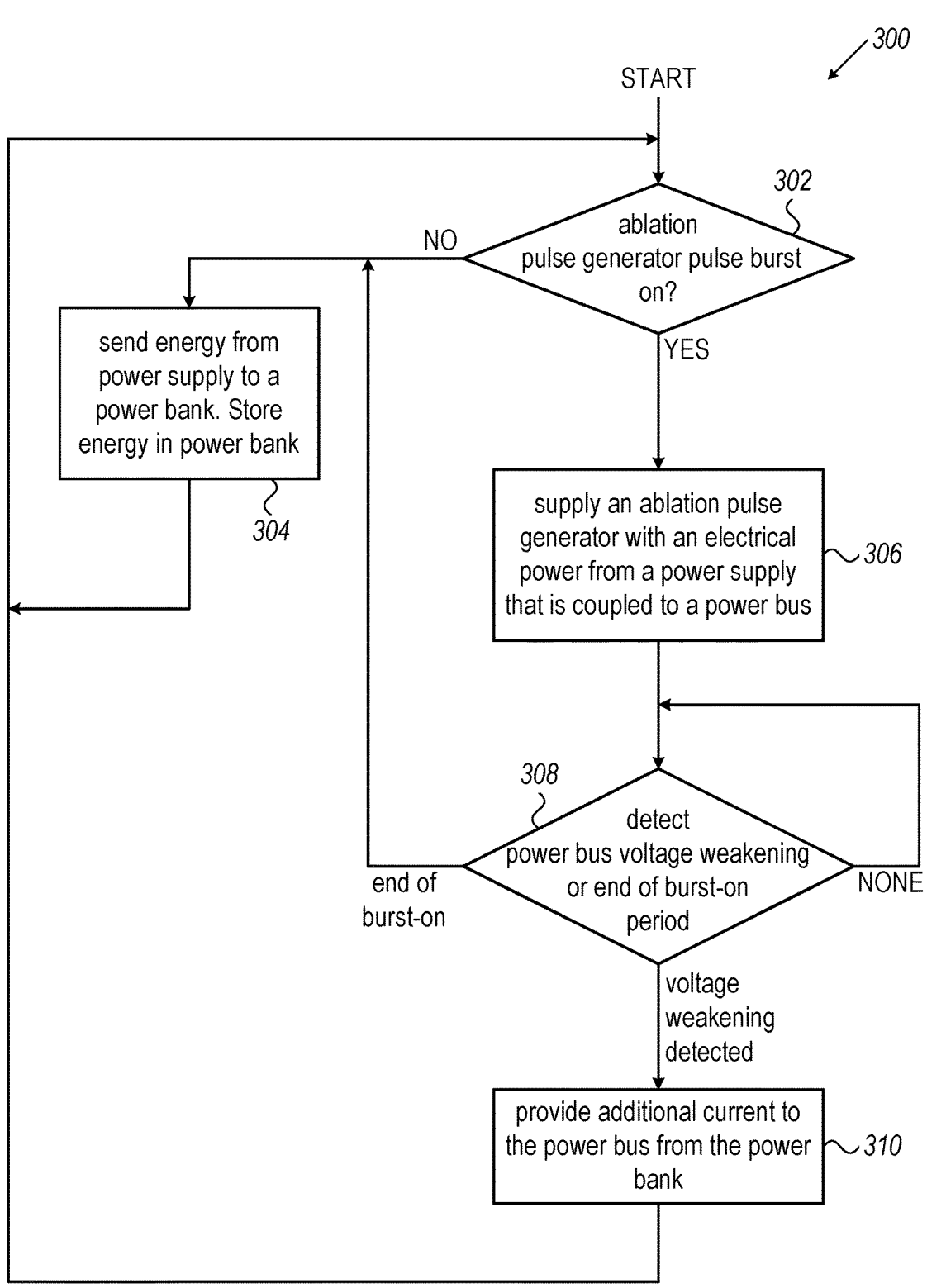
FIG. 4 is a flowchart that schematically illustrates a method for providing power to an ablation pulse generator, in accordance with an example of the present disclosure.

FIG. 4 is a flowchart that schematically illustrates a method 300 for providing power to an ablation pulse generator, in accordance with an example of the present disclosure. The flowchart is executed by ablation energy generator 50 (FIG. 2) and the subcircuits thereof.

The flowchart starts at a check-ablation-burst-on step 302, wherein the ablation energy delivery circuit checks whether the ablation pulse generator is currently generating a burst of ablation pulses. If the ablation pulse generator does not currently generate a burst of ablation pulses, the flowchart will enter a send-energy-to-power-bank step 304, wherein the current output of the power supply charges the capacitors of the power bank.

If, in step 302, the ablation pulse generator does generate a burst of ablation pulses, the flowchart will enter a supply-current-from-power-supply step 306, wherein the power supply delivers power through the power bus to the ablation pulse generator, and then proceed to a detect-voltage-weakening-or-end-of-burst step 308.

In some cases (depending on the ohmic resistance of the tissue being ablated) the power that the power supply supplies to the ablation pulse generator may not suffice. When this happens, the voltage on the power bus will gradually weaken. Sensing circuit 110 will, in step 308, detect such weakening. The sensing circuit measures the voltage on the power bus. In some examples, the sensing circuit compares the voltage to a preset threshold, and signals voltage weakening when the voltage is below the threshold. In other examples, the sensing circuit detects voltage weakening when the rate of decline of the power bus voltage (e.g., in volt/second) is above a preset threshold.

Additionally, while in step 308, the ablation generator checks if the ablation pulse generator is still sending pulses and, hence, consumes high power. If the pulse burst has stopped, the flowchart will reenter step 304, to store energy in the power bank.

If, in step 308, the sense circuit detects weakening of the voltage on the power bus, the flow chart will enter a provide-additional-current step 310, wherein the power bank augments the current that the power supply delivers, to match the requirement of the ablation pulse generator, and then reenter step 302.

If, in step 308, the sense circuit does not sense a weakening of the voltage, and the ablation pulse burst is still on, the flowchart remains in step 308.

Flowchart 300 is cited by way of example merely for the sake of conceptual clarity. Other flowcharts may be used in other aspects. For example, in an aspect, there is no sense circuit, the power bank charges when there is no burst of ablation pulses and augments the power supply when a burst is on; the flowchart changes accordingly.

The configurations of ablation energy delivery system 50, including ablation pulse generator 102, power supply 104, power bank 108 and sensing circuit 110; the curves of diagram 200 and the method of flowchart 300, illustrated in FIGS. 1 through 4 and described hereinabove, are example configurations, waveforms and flowcharts that are shown purely for the sake of conceptual clarity. Any other suitable configurations, waveforms and flowcharts can be used in alternative examples.

Processor 77 (FIG. 1) may comprise one or more general-purpose processors, which are programmed in software to carry out the functions described herein. The software may be downloaded to the processor in electronic form, over a network or from a host, for example, or it may, alternatively or additionally, be provided and/or stored on non-transitory tangible media, such as magnetic, optical, or electronic memory.

Although the example described herein mainly address delivery of power to an ablation pulse generator, the methods and systems described herein can also be used in other applications.

EXAMPLES

Example 1: An apparatus (50) for generating ablation pulses includes a pulse generator (102), a power supply (104), a sensing circuit (110), and an energy storage power bank (108). The pulse generator is configured to generate ablation pulses for ablation of tissue. The power supply is configured to supply electrical power to the pulse generator. The sensing circuit is configured to sense a weakening of the electrical power supplied by the power supply to the pulse generator. The energy storage power bank is connected in parallel with the power supply, and is configured to supply to the pulse generator, responsively to an indication from the sensing circuit indicative of the weakening, additional current that augments a current supplied by the power supply.

Example 2: The apparatus according to example 1, wherein the energy storage power bank includes a high-energy capacitor configured to store an electrical charge.

Example 3: The apparatus according to example 1, wherein the sensing circuit is configured to sense the weakening by sensing a voltage level supplied by the power supply.

Example 4: The apparatus according to example 1, wherein the sensing circuit is configured to sense the weakening by detecting a decrease in a voltage level supplied by the power supply.

Example 5: The apparatus according to example 1, wherein the sensing circuit is configured to sense the weakening by detecting a rate of decrease in a voltage level supplied by the power supply.

Example 6: The apparatus according to example 1, wherein the pulse generator is configured to generate intermittent bursts of the ablation pulses.

Example 7: The apparatus according to example 6, wherein the power supply is configured to charge the energy storage power bank with energy during time intervals between the bursts.

Example 8: The apparatus according to example 1, wherein the sensing circuit is integrated in the energy storage power bank.

Example 9: A method for generating ablation pulses includes generating ablation pulses using a pulse generator, for ablation of tissue, and supplying electrical power to the pulse generator by a power supply. A weakening of the electrical power, supplied by the power supply to the pulse generator, is sensed. Additional current, which augments a current supplied by the power supply, is supplied to the pulse generator using an energy storage power bank that is connected in parallel with the power supply, responsively to the sensed weakening of the supplied electrical power.

It will thus be appreciated that the examples described above are cited by way of example, and that the invention is not limited to what has been present particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. An apparatus for generating ablation pulses, the apparatus comprising:

a pulse generator, configured to generate ablation pulses for ablation of tissue in intermittent bursts of the ablation pulses with time intervals between the bursts;

a power supply, configured to supply electrical power to the pulse generator during generation of the intermittent burst and to charge an energy storage power bank during the time intervals between bursts, wherein the power supply is connected via an AC plug to mains electricity;

a sensing circuit, configured to sense a weakening of the electrical power supplied by the power supply to the pulse generator during generation of the ablation pulses and provide an indication based on the sensed weaking; and the energy storage power bank, which is connected in parallel with the power supply and is configured to supply to the pulse generator, responsively to the indication, additional current that augments a power supply output current supplied by the power supply.

2. The apparatus according to claim 1, wherein the energy storage power bank comprises a high-energy capacitor configured to store an electrical charge.

3. The apparatus according to claim 1, wherein the sensing circuit is configured to provide the indication based on sensing a voltage level supplied by the power supply.

4. The apparatus according to claim 1, wherein the sensing circuit is configured to provide the indication based on detecting a decrease in a voltage level supplied by the power supply.

5. The apparatus according to claim 1, wherein the sensing circuit is configured to provide the indication based on a rate of decrease in a voltage level supplied by the power supply that is sensed by the sensing circuit during at least one of the intermittent bursts.

6. The apparatus according to claim 1, wherein charging the energy storage power bank with energy from the power supply is initiated based on power supply current consumption dropping to zero for a period of time greater than a predefined threshold.

7. The apparatus according to claim 1, wherein the sensing circuit is integrated in the energy storage power bank.

8. A method for generating ablation pulses, the method comprising:
   generating ablation pulses using a pulse generator, for ablation of tissue in intermittent bursts of the ablation pulses with defined time intervals between the bursts;
   supplying electrical power to the pulse generator by a power supply during generation of the intermittent burst, wherein the power supply is connected via an AC plug to mains electricity;
   sensing a weakening of the electrical power supplied by the power supply to the pulse generator during generation of the ablation pulses;
   generating an indication based on sensing the weakening of the electrical power supplied by the power supply;
   using an energy storage power bank that is connected in parallel with the power supply to augment the current that the power supply delivers, supplying to the pulse generator, responsively to detecting the indication, additional current that augments a power supply output current supplied by the power supply; and charging the energy storage power bank during the time intervals between bursts.

9. The method according to claim 8, wherein the energy storage power bank comprises a high-energy capacitor configured to store an electrical charge.

10. The method according to claim 8, wherein providing the indication is based on sensing a voltage level supplied by the power supply.

11. The method according to claim 8, wherein providing the indication is based on detecting a decrease in a voltage level supplied by the power supply.

12. The method according to claim 8, wherein providing the indication is based on detecting a rate of decrease in a voltage level supplied by the power supply.

13. The method according to claim 8, wherein charging the energy storage power bank with energy is initiated based on power supply current consumption of the pulse generator dropping to zero for a period of time greater than a predefined threshold.

14. The method according to claim 8, wherein sensing of the weakening is performed by a sensing circuit that is integrated in the energy storage power bank.

15. The apparatus of claim 1, further comprising a power bus, wherein the power-supply, the power bank and the sensing circuit are coupled to the power bus and wherein the weakening is weakening of voltage sensed on the power bus during a burst-on period of the pulse generator.

16. The apparatus of claim 15, wherein the power supply is configured to switch from supplying electrical power to the pulse generator to charging the energy storage power bank based on the sensing circuit sensing an end of the burst-on period.

17. The method of claim 8, further comprising a power bus, wherein the power-supply, the power bank and the sensing circuit are coupled to the power bus and wherein the weakening is weakening of voltage sensed on the power bus during a burst-on period of the pulse generator.

18. The apparatus of claim 17, wherein the power supply is configured to switch from supplying electrical power to the pulse generator to charging the energy storage power bank based on the sensing circuit sensing an end of the burst-on period.

* * * * *